United States Patent [19]
Bogart et al.

[11] Patent Number: 6,104,948
[45] Date of Patent: *Aug. 15, 2000

[54] METHOD FOR VISUALLY INTEGRATING MULTIPLE DATA ACQUISITION TECHNOLOGIES FOR REAL TIME AND RETROSPECTIVE ANALYSIS

[75] Inventors: Edward H. Bogart, Hampton; Alan T. Pope, Poquoson, both of Va.

[73] Assignee: The United States of America as represented by the Administrator of the National Aeronautics and Space Administration, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/641,041

[22] Filed: Apr. 3, 1996

[51] Int. Cl.$^7$ ........................................................ A61B 5/04
[52] U.S. Cl. ......................... 600/524; 600/301; 600/483; 600/544
[58] Field of Search .................... 128/920, 922, 128/731, 732, 670, 700, 710–712, 923; 600/300, 301, 483, 513, 509, 544, 545, 523, 524

[56] References Cited

U.S. PATENT DOCUMENTS

| | | |
|---|---|---|
| 4,804,950 | 2/1989 | Moon et al. . |
| 5,200,744 | 4/1993 | Hiromoto et al. . |
| 5,250,933 | 10/1993 | Beaudin et al. . |
| 5,377,100 | 12/1994 | Pope et al. . |
| 5,400,792 | 3/1995 | Hoebel et al. ............................ 128/670 |
| 5,406,306 | 4/1995 | Siann et al. . |
| 5,406,792 | 4/1995 | Tansey .................................... 128/732 |
| 5,434,590 | 7/1995 | Dinwiddie, Jr. et al. . |
| 5,441,047 | 8/1995 | David et al. ............................. 128/670 |
| 5,447,164 | 9/1995 | Shaya et al. ............................. 128/710 |
| 5,553,609 | 9/1996 | Chen et al. .............................. 600/301 |
| 5,619,995 | 4/1997 | Lobodzinski ............................. 600/301 |

OTHER PUBLICATIONS

Pope et al, "Biccybernetic system validates index of operator engagement in automated task", Biological Physchology, vol. 40, Nos. 1 and 2, May 1995, pp. 300–306.

Bogart et al, "Contingent control of cognitive engagement", Physchophysiology, vol. 30, Supplement 1, Society for Physhophysiological Research Thrity–Third Annual Meeting, Oct. 27–31, 1993, Rottach–Egern, Germany, vol. 30, Aug. 1993, 2 pgs.

Pope et al., "Identification of hazardous awareness states in monitoring environments",SAE 1992 Transactions Journal of Aerospace, Section 1–vol. 101, 921136, 1992, 9 pgs.

Pope et al, "Extended attention span training system", NASA Conference Publication 3136, vol. 1, Technology 2001 Conference Proceedings, Dec. 3–5, 1991, pp. 368–374.

Primary Examiner—George R. Evanieko
Attorney, Agent, or Firm—Robin W. Edwards

[57] ABSTRACT

A system for display on a single video display terminal of multiple physiological measurements is provided. A subject is monitored by a plurality of instruments which feed data to a computer programmed to receive data, calculate data products such as index of engagement and heart rate, and display the data in a graphical format simultaneously on a single video display terminal. In addition live video representing the view of the subject and the experimental setup may also be integrated into the single data display. The display may be recorded on a standard video tape recorder for retrospective analysis.

14 Claims, 2 Drawing Sheets

METHOD FOR VISUALLY INTEGRATING MULTIPLE DATA ACQUISITION TECHNOLOGIES FOR REAL TIME AND RETROSPECTIVE ANALYSIS

ORIGIN OF THE INVENTION

The invention described herein was jointly made by an employee of the United States Government and by a contractor during the performance of work under a NASA contract and is subject to provisions of Section 305 of the National Aeronautics and Space Act of 1958, as amended, Public Law 85-568 (72 Stat. 435; 42 USC 2457).

BACKGROUND OF THE INVENTION

1. Technical Field of the Invention

The present invention relates generally to experimental data collection, display and analysis and specifically to gathering, organizing and visually displaying information from multiple data sources.

2. Discussion of the Related Art

When designing devices for use by human operators it is useful to determine how an individual will interact with the new device. One method of doing this quantitatively is to monitor certain physical reactions by the operator such as heart rate, skin temperature, gross physical movements of the operator and where the subject is looking. In most cases this is done by using several separate machines, each with its own display medium and recording facility. This requires an experimenter to attend to several different data displays of different types and formats which may be physically distant from each other. A further drawback of multiple monitoring systems is that retrospective analysis of the data requires time synchronization of the several types of data recordings which may be difficult.

Another factor that may be observed to study the interaction between an operator and a device is an index of engagement. During operation of a task set, electroencephalographic (EEG) signals may be used to reflect an operator's engagement in the task set. An index of engagement may be defined that is an indication of the operator's engagement. One such index, using EEG signals, defined as beta power/(alpha power+theta power) was found to be a useful engagement index in a paper by Pope, Alan T., Bogart, Edward H. and Bartolome, Debbie S., "Biocybernetic system evaluates indices of operator engagement in automated task," Biological Psychology 40 (1995) 187–195.

This engagement index may be used to design a negative feedback system for monitoring of automated tasks such that as an operator is found to have decreased attention, the level of automation is reduced. The reduction in automation levels means that there is an increased task demand on the operator which increases the operator's level of engagement. Similarly a positive feedback system may be employed such that as the operator's level of engagement drops, the automation level of the tasks is increased, decreasing the demand on the operator. A negative feedback system produces stable short-cycle oscillation in engagement index while a positive feedback system produces longer, more variable periods of oscillation in engagement index.

Others have produced products or patents dealing with the problem of displaying multiple signals in a single display.

Telefactor Corp. of W. Conshohocken, PA produces a device for the collection and display of multiple EEG or electrocardiograph (ECG) signals. It includes video output capability to standard video tape recorders and the ability to superimpose waveforms onto a video signal.

Hiromoto et. al. (U.S. Pat. No. 5,200,734) disclose a system for monitoring a plant in which a plurality of interactive functions for control of a plant are displayed on a screen simultaneously. The system uses discriminating means to determine which interactive functions are displayed and in which order they are presented so that the most likely functions to be used are readily available to the user. The data used by the discriminating means are collected from a plurality of monitoring devices and processed in a computer.

Beaudin et. al. (U.S. Pat. No. 5,250,933) disclose a system for simultaneous display of multiple images on a single video display device. The system of the '933 patent is a windowing system that allows for windowing of digital or analog video and for independent color mapping for each window. This system incorporates the ability to read from or output to a video tape recorder (hereafter VTR) so that retrospective analysis of the images may be made.

Dinwiddie Jr. et. al. (U.S. Pat. No. 5,434,590) disclose a multimedia system for simultaneous display of multiple image signals, including full motion video signals, the image signals derived from a plurality of media sources. Image signals pass through a media bus to a media control module which, in turn provides a composed image signal to a display device.

Siann et. al. (U.S. Pat. No. 4,406,306) disclose a system for displaying information from a graphics memory and a video memory on a display monitor. The graphics data is displayed on the display monitor and the video data is displayed in a window in the display monitor.

Moon et. al. (U.S. Pat. No. 4,804,950) disclose a system for multichannel data acquisition and display for signal monitoring. The system of the '950 patent is used for patient monitoring by a plurality of devices. The data from the monitoring instruments passes through dedicated module and channel tables which in turn supply the data to display windows in a single display device.

SUMMARY OF THE INVENTION

It is an object of the present invention to provide a method of visually integrating data and data products from various data acquisition technologies for real time and retrospective analysis.

It is an additional object of the present invention to provide synchronized data display, on a single video display terminal (hereafter VDT), for types of data including but not limited to: date and time, electrophysiological data and data products such as index of engagement, oculometer derived look-point superimposed on scene video, and video view the subject's movements in an experimental setup.

It is an additional object of the present invention to allow video recording of the combined data display to allow for quick retrospective analysis and for storage of the data.

To achieve the forgoing objects, a computer is provided. The computer being capable of supporting input of multiple channels of video with sound and output of video to a standard VTR, input of several data channels in the form of analog or digital voltages, and storage of data and data products to magnetic or optical media. In addition, the computer should be capable of displaying the multiple channels of video and combining them with the other displays on the VDT. For example, a desk top computer such as an Apple Macintosh is appropriate to this application. An additional advantage of this type of computer is the ability to manipulate display windows, minimizing those windows which are not important at a given instant or rearranging them to better emphasize particular portions of the display.

A system of software is provided, the software capable of receiving incoming analog or digital data streams from input interface hardware, converting raw data to data products as required, displaying raw data or data products on a VDT in the form of digital displays, readouts, graphs and charts, and generating an elapsed-time or real time clock display. For example, LabVIEW is a commercially available product that may be appropriately programmed to perform the above activities. Finally an output interface is provided to convert the VDT display to standard video output that may be recorded on a standard VTR.

DESCRIPTION OF PREFERRED EMBODIMENTS

An operator of an experimental setup and parameters in the experimental apparatus are monitored by a system according to the present invention.

Figure 1:
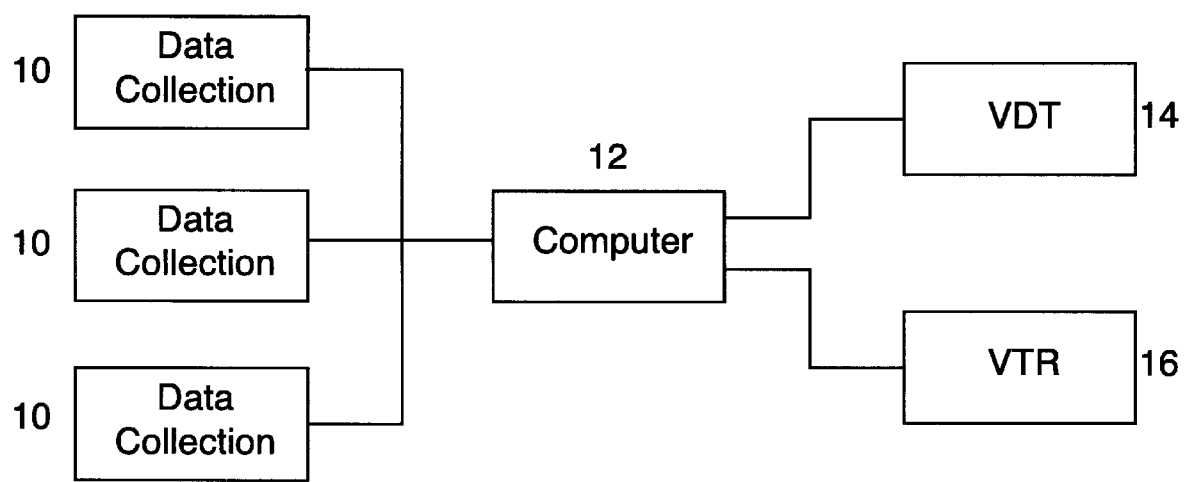
FIG. 1 is a block diagram according to the present method.
Figure 2:
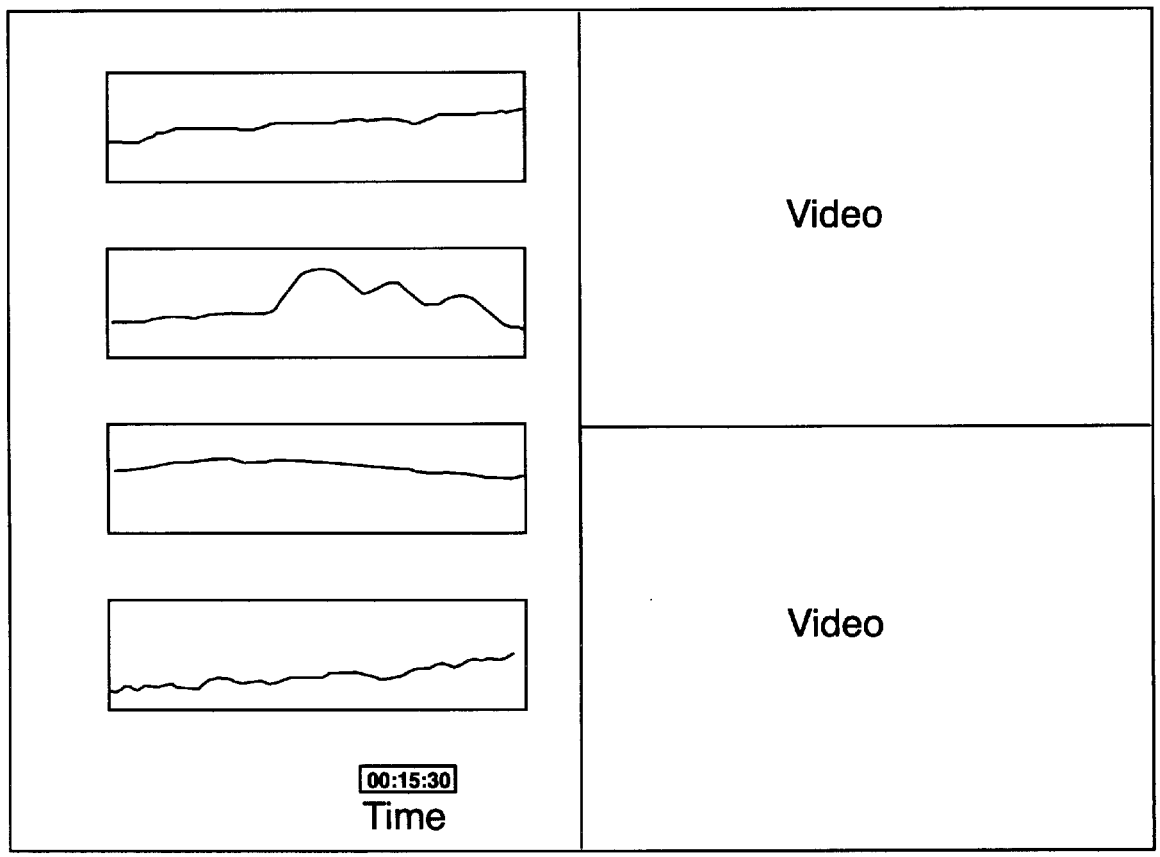
FIG. 2 is a drawing showing an integrated video display including graphs of data and data products, video and clock.

Referring to FIG. 1, and FIG. 2 data from the operator during performance of a task set are collected by a plurality of data collection means 10. Preferred types of data include EEG and ECG data, skin conductance information, skin temperature, elapsed time, digital status line, oculometer derived look-point data, video of the scene and video of the the subject moving in the experimental setup.

Data from the plurality of data collection means is collected in a computer 12 and stored in the computer memory. Data may then be processed into further data products. These data products include an index of engagement and heart rate. Index of engagement may be calculated by first calculating EEG power in three power bands (theta, alpha and beta) where alpha is defined to be 8–13 Hz, beta 13–22 Hz and theta 4–8 Hz. It is beneficial to use the sum of the power from each of several sites. Exemplary sites are Cz, Pz, P3 and P4 as defined by the International 10-20 system. These are sites known to be involved in attention and vigilance. The power in each of the three bands is processed to provide an engagement index according to the EEG literature. An index that has been found to reflect engagement well is beta power divided by the sum of alpha and theta power.

Heart rate may be calculated from ECG data. As ECG data vectors are read in they are checked for the presence of an R wave. By counting elapsed time between R waves a heart rate may be calculated. It is also of use to use a discriminating algorithm to remove calculated values for heart rate that appear to be incorrect. When such a heart rate is thrown out the previous good rate may be substituted as a reasonable approximation. For example, rates above 120 or below 30 may be discounted as incorrect values in a trial where there is no expectation of very high or very low values. Most heart rate calculations are performed by monitoring the ECG signal for waves that surpass a preselected threshold level. By this method R waves may be identified at the rising edge. The present invention makes use of peak detection rather than a threshold. Thus heart rate may be calculated from time between measured peaks.

Other data must be processed before display steps. For example, a skin temperature probe may produce a voltage signal that must be calibrated to provide skin temperature data. The same software that is used to produce data products such as the index of engagement and heart rate may be used to process temperature voltages to produce temperature in common units such as degrees Fahrenheit. All data should be processed simultaneously so that they may be displayed in a synchronized manner.

It is preferable that each type of data be processed in an individual software module and that the overall software system be built from these individual software modules. This is advantageous in that simply by choosing a different set of modules and corresponding data collection means, the method of the present invention may be easily be adapted to different uses.

Data processed in the computer are then displayed on a VTR 14. In addition, data is preferably stored in computer long term memory such as magnetic media or optical media. Some data such as index of engagement and temperature are displayed in graphical form. A plurality of data are displayed simultaneously to provide synchronization. That is, each graph is calibrated so that data from different sources displayed at a given time corresponds to data collected concurrently. For example, this means that scene video should be displayed simultaneously with a heart rate and index of engagement corresponding to the operator's heart rate and index of engagement at the same time that the scene video was taken. Preferably acquisition, processing and display take place in real time so that at any instant the display corresponds to the physiology of the operator at that instant.

Output interface means is provided to convert a VDT display signal to a standard video output signal such as NTSC that may be recorded on a standard VTR 16. The signal is recorded on a VTR so that it may be analyzed retrospectively.

In retrospective analysis the VTR recording provides a method of examining data in a low time-resolution manner. The data as stored in the magnetic or optical media is in a high time-resolution form. By first examining the VTR recording a quick determination may be made as to which portions of the higher resolution data should be further examined.

Other variations will be readily apparent to those of skill in the art. The forgoing is not intended to be an exhaustive list of modifications but rather is given by way of example. It is understood that it is in no way limited to the above embodiments, but is capable of numerous modifications within the scope of the following claims.

What is claimed is:

1. A method for using a computer having a long term memory and a system of software to visually integrate multiple data acquisition technologies for real time and retrospective analysis comprising:

collecting physiological data of a subject from a plurality of data collecting means;

collecting live scene video data representing the subject's view from the plurality of data collecting means;

accepting the physiological data and the live scene video data into the computer;

storing the physiological data and the live scene video data in the long term memory of the computer;

converting the physiological data to physiological data products with the system of software;

combining the physiological data products and live scene video data into a synchronized integrated video signal;

producing the synchronized integrated video signal on a video display terminal;

passing the synchronized integrated video signal to a video tape recorder; and storing the synchronized integrated video signal on the video tape recorder for the retrospective analysis.

2. The method of claim 1 wherein the live scene video data further comprises live video of the subject.

3. A method for using a computer having a long term memory and a system of software to visually integrate multiple data acquisition technologies for real time and retrospective analysis comprising:

collecting EEG data of a subject from a plurality of data collecting means;

collecting ECG data of the subject from the plurality of data collecting means;

collecting live scene video data representing the subject's view from the plurality of data collecting means;

accepting the EEG data, the ECG data, and the live scene video data into the computer;

converting simultaneously the EEG data into an index of engagement data with the system of software, and the ECG data into a heart rate data with the system of software;

combining the index of engagement data, the heart rate data, and the live scene video data into a synchronized integrated video signal;

producing the synchronized integrated video signal on a video display terminal;

passing the synchronized integrated video signal to a video tape recorder; and storing the synchronized integrated video signal on the video tape recorder for the retrospective analysis.

4. The method of claim 2 further comprising storing the EEG data, the ECG data, the index of engagement data, and the heart rate data in the long term memory of the computer.

5. The method of claim 3 wherein the step of converting each type of data further comprises:

passing each type of data to an individual software module;

processing each type of data in each individual software module;

building a modular software system from the individual software modules; and including the modular software system in the system of software.

6. The method of claim 3 wherein the live scene video data further comprises live video data of the subject.

7. The method of claim 6 wherein the data provided by the EEG data collecting means, the data provided by the ECG data collecting means, the index of engagement data, and the heart rate data are stored in the long term memory.

8. The method of claim 6 wherein the system of software further comprises a modular software system wherein each type of data is processed in an individual software module and that the system of software is built from the individual software modules.

9. A method for using a computer having a long term memory and a system of software to visually integrate multiple data acquisition technologies for real time and retrospective analysis comprising:

collecting EEG data of a subject from a plurality of data collecting means;

collecting ECG data of the subject from the plurality of data collecting means;

collecting look point data of the subject from the plurality of data collecting means;

collecting skin conductance data of the subject from the plurality of data collecting means;

collecting live scene video data representing the subject's view from the plurality of data collecting means;

accepting the EEG data, the ECG data, the look point data, the skin conductance data, and the live scene video data into the computer;

converting simultaneously the EEG data into an index of engagement data with the system of software, and the ECG data into a heart rate data with the system of software;

combining the look point data and the live scene video data into a look point video;

combining the index of engagement data, the heart rate data, the skin conductance data, the look point video, and the live scene video data into a synchronized integrated video signal;

producing the synchronized integrated video signal on a video display terminal;

passing the synchronized integrated video signal to a video tape recorder; and storing the synchronized integrated video signal for retrospective analysis.

10. The method of claim 9 further comprising storing the EEG data, the ECG data, the index of engagement data, the heart rate data, and the skin conductance data in the long term memory of the computer.

11. The method of claim 9 wherein the step of converting each type of data further comprises:

passing each type of data to an individual software module;

processing each type of data in each individual software module;

building a modular software system from the individual software modules; and including the modular software system in the system of software.

12. The method of claim 9 wherein the live scene video data further comprises live video of the subject.

13. The method of claim 12 wherein the data provided by the EEG data collecting means, the data provided by the ECG data collecting means, the index of engagement data, the heart rate data, and the skin conductance data are stored in the long term memory.

14. The method of claim 12 wherein the system of software further comprises a modular software system wherein each type of data is processed in an individual software module and that the system of software is built from the individual software modules.

* * * * *